United States Patent [19]

Lorincz

[11] Patent Number: 4,849,332

[45] Date of Patent: Jul. 18, 1989

[54] HUMAN PAPILLOMAVIRUS 35 NUCLEIC ACID HYBRIDIZATION PROBES AND METHODS FOR EMPLOYING THE SAME

[75] Inventor: Attila T. Lorincz, Gaithersburg, Md.

[73] Assignee: Life Technologies, Inc., Gaithersburg, Md.

[21] Appl. No.: 53,776

[22] Filed: May 26, 1987

[51] Int. Cl.[4] .......................... C12Q 1/70; C12Q 1/68; G01N 33/53; C07H 15/12

[52] U.S. Cl. ........................................... 435/5; 435/6; 435/7; 435/21; 435/28; 435/172.1; 435/948; 436/501; 536/26; 536/27; 536/28; 935/77; 935/78

[58] Field of Search ..................... 435/6, 7, 5, 21, 28, 435/172.1, 948; 436/501; 536/26–28; 935/87, 88

[56] References Cited

PUBLICATIONS

Milde, K., et al., J. Oral Pathol. 15:292–296 (1986).
Loring, A., et al., Banbury Report 21, Cold Spring Harbor Laboratory pp. 225–237 (1986).
zur Hausen, H., et al., Prog. Med. Virol. 32:15–21 (1985).
Beaudenon, S. et al, Nature, 321:246–249 (1986).
Lorincz, A. T. et al, J. Virol., 58:225–229 (1986).
Lorincz, A. T. et al, Virol., 159:187–190 (1987).

*Primary Examiner*—Robert J. Warden
*Assistant Examiner*—Jack Spiegel
*Attorney, Agent, or Firm*—Sughrue, Mion, Zinn, Macpeak & Seas

[57] ABSTRACT

Nucleic acid hybridization probes for human papillomavirus types and particularly human papillomavirus type 35; and methods for employing the same.

94 Claims, 2 Drawing Sheets

HUMAN PAPILLOMAVIRUS 35 NUCLEIC ACID HYBRIDIZATION PROBES AND METHODS FOR EMPLOYING THE SAME

FIELD OF THE INVENTION

The present invention relates to nucleic acid hybridization probes for human papillomavirus types and particularly for human papillomavirus type 35 (hereinafter "HPV 35"); and methods for employing the same.

BACKGROUND OF THE INVENTION (A) Human Papillomavirus Types

Human papillomaviruses (hereinafter "HPV") are recognized as a cause of various epithelial lesions such as warts, condylomas and dysplasias (see Gissmann, L., Cancer Surv., 3: 161 (1984); Pfister, H., Biochem. Pharmacol., 99: 111 (1983); Durst, M. et al, Proc. Natl. Acad. Sci. USA, 80: 3812 (1983) and Boshart, M. et al, EMBO J., 3:1151 (1984)). Dysplasias of the cervix (also known as cervical intraepithelial neoplasia (CIN)) are believed to be early events in the progression to cervical cancer; the progression proceeding from mild dysplasia (CIN I), to moderate dysplasia (CIN II), to severe dysplasia, to carcinoma in situ (collectively CIN III), to invasive cancer.

Studies examining the association of HPV type with dysplasias of the cervix and cancer of the cervix have shown that HPV types 6, 11 16, 18, 31 and 33 are associated with a high percentage of genital lesions (see Gissmann, L., Cancer Surv., 3: 161 (1984); Pfister H., Biochem. Pharmacol., 99: 111 (1983); Durst, M. et al, Proc. Natl. Acad. Sci. USA, 80: 3812 (1983); Boshart, M. et al, EMBO J., 3: 1151 (1984); de Villiers, E. -M. et al, J. Virol., 40: 932 (1981); Gissmann, L. et al, J. Virol., 44: 393 (1982); Lorincz, A. T. et al. J. Virol., 58: 225 (1986) and Beaudenon, S., Nature, 321: 246 (1986)).

HPVs are grouped into types based on the similarity of their DNA sequence. Two HPVs are taxonomically classified as being of the same type if their DNAs cross-hybridize to greater than 50%, as measured by hybridization in solution under moderately stringent hybridization conditions, which are defined as approximately 25° C. below the melting temperature of a perfectly base-paired double-stranded DNA (conveniently written as $T_m-25°$ C.), followed by chromatography on hydroxyapatite to separate double-stranded DNA from single-stranded DNA (see Coggin, J. R. et al, Cancer Res., 39: 545 (1979)). The melting temperature ($T_m$) of a perfectly base-paired double-stranded DNA can be accurately predicted using the following well established formula:

$$T_m = 16.6 \times \log [Na^+] + 0.41 \times \%G:C + 81.5 - 0.72 \times (\%)(v/v) \text{ formamide.}$$

The above formula provides a convenient means to set a reference point for determining non-stringent and stringent hybridization conditions for various DNAs in solutions having varying salt and formamide concentrations without the need for empirically measuring the $T_m$ for each individual DNA in each hybridization condition.

If less than 50% of the respective HPV DNAs are able to cross-hybridize in solution under moderately stringent conditions to form fully or partially double-stranded structures, as measured and defined by the ability to bind to hydroxyapatite, then the HPV DNAs are not sufficiently related to be taxonomically classified as being of the same type. A cut-off of 50% cross-hybridization using this method is employed as the consensus criterion for the assignment of novel HPV types for nomenclature purposes. This method for measuring the degree of cross-hybridization between HPV DNAs has been historically adopted as the method to be used to determine whether two HPV DNAs represent different isolates of a common type or represent isolates of different types. The use of this criterion pre-dates the establishment of clinical criterion for determining and defining HPV types. As discussed in more detail below, the clinical criterion for determining and defining HPV types is based upon the epidemiological distribution of HPV types among genital lesions.

The above-described method of measuring the degree of cross-hybridization is based on an assessment of the extent of formation of fully or partially double-stranded DNA molecules after the hybridization reaction. However, it should be noted that conversion of 50% of the DNAs into fully or partially double-stranded DNA molecules does not imply that the nucleotide sequences of the DNAs are 50% homologous.

As discussed above, HPVs can also be grouped into types based on clinical criterion. That is, it has been observed that HPV of different types, as defined by the degree of cross-hybridization criterion described above, show distinct epidemiological distributions among genital lesions of different severities and among different geographic populations.

For example, HPV 6 and HPV 11 are principally associated with benign lesions such as exophytic condylomas and to a lesser extent with flat condylomas (see Gissmann, L. et al, Proc. Natl. Acad. Sci., USA, 80: 560 (1983)). HPV 6 and HPV 11 are also detected in certain rare types of malignant epithelial tumors (see Zachow, K. R. et al, Nature, 300: 771 (1982) and Rando, R. F., J. Virol., 57: 353 (1986)). In contrast, HPV 16, HPV 18, HPV 31 and HPV 33 are detected with varying degrees of frequency in cervical and other anogenital cancers as well as their precursor lesions (see Durst, M. et al, Proc. Natl. Acad. Sci., USA, 80: 3812 (1983), Boshart, M. et al, Embo. J., 3: 115 (1984), Lorincz, A. T. et al, J. Virol., 58: 225 (1986) and Beaudenon, S., Nature, 321: 246 (1986)). This distribution of HPV 16, HPV 18, HPV 31 and HPV 33 is believed to reflect a greater risk of, or a more rapid progression to, cervical cancer arising from genital lesions infected with HPV 16, HPV 18, HPV 31 and HPV 33 as compared to lesions infected with HPV 6 and HPV 11. As a result, the determination of HPV types has clinical-diagnostic value, i.e., such is an important factor in the assessment of risk of cancer development in patients who exhibit evidence of HPV infection. Based on the assessed risk of cancer development, appropriate therapeutic treatments can be selected.

In addition, HPV 16 is more prevalent in Europe than in Africa (Durst, M. et al, Proc. Natl. Acad. Sci., USA, 80: 3812 (1983)), whereas HPV 18 is more prevalent in Africa than in Europe (Boshart, M. et al, EMBO J., 3: 1115 (1984)).

Accordingly, within the context of the present invention, two HPVs are considered to be of the same type if either (1) they meet the criterion for the degree of cross-hybridization discussed above or (2) if they show substantially the same epidemiological distribution of cross-hybridization among genital lesions and they both cross-hybridize with the same genital lesions which comprise the epidemiological distribution.

It has been found that a significant percentage of cervical cancer and genital lesions which have the potential to progress to cervical cancer contain "new" HPV types which do not correspond to any of the known HPV types. Thus, in light of the known association of specific HPV types with genital lesions which have a high risk of progression to cervical cancer, the ability to detect and group these "new" HPV types allow the risk of cervical cancer associated with these "new" HPV types to be ascertained in patients who exhibit evidence of HPV infection and who may be infected with these "new" HPV types.

(B) Cloning of HPV Types

In spite of long standing efforts in the art, it has not been possible to propagate HPV in cell culture in vitro. However, recombinant DNA cloning techniques have made it possible to isolate and purify the DNA of many HPV types such as HPV Types 6, 11, 16, 18, 31 and 33 (see Durst, M. et al, *Proc. Natl. Acad. Sci. USA*, 80: 3812 (1983); Boshart, M. et al, *EMBO J.*, 3: 1151 (1984); de Villiers, E.-M. et al, *J. Virol.*, 40: 932 (1981); Gissmann, L. et al, *J. Virol.*, 44: 393 (1982); Lorincz, A. T. et al *J. Virol.*, 58: 225 (1986) and Beaudenon, S., *Nature*, 321: 246 (1986)). Most of the knowledge regarding HPVs has been derived from the study of the DNA sequence in such recombinant DNAs and the use of these DNAs to prepare nucleic acid hybridization probes for detection of HPV in tissue samples.

(C) Hybridization Probes

As discussed above, HPV DNA has been employed as hybridization probes to differentiate HPV types. Two HPV DNAs of different types can be readily distinguished by hybridization under stringent hybridization conditions, which are defined as approximately 10° C. below the melting temperature of a perfectly based-paired double-stranded DNA hybrid (conveniently written as $T_m - 10°$ C.), using such hybridization probes. Similarly, an HPV DNA of one type can be readily distinguished from an HPV RNA of another type by hybridization under stringent hybridization conditions which are defined as approximately 10° C. below the melting temperature of a perfectly based-paired double-stranded DNA-RNA hybrid (conveniently written as $T_m - 10°$ C.), using such hybridization probes. Further, two HPV RNAs of different types can be readily distinguished by hybridization under stringent hybridization conditions, which are defined as approximately 10° C. below the melting temperature of a perfectly based-paired double-stranded RNA-RNA hybrid (conveniently written as $T_m - 10°$ C.), using such hybridization probes. It should be noted that HPV DNAs or RNAs which are designated as different types using the above criterion, may in fact have as much as 80% of their nucleotide sequences in common.

Furthermore, two HPV DNAs of different types are able to cross-hybridize under non-stringent hybridization conditions, which are defined as approximately 35° C. or more below the melting temperature of a perfectly base-paired double-stranded DNA-DNA hybrid (conveniently written as $T_m - 35°$ or more), using such hybridization probes. Similarly, an HPV DNA of one type is able to cross-hybridize with an HPV RNA of another type by hybridization under non-stringent hybridization conditions which are defined as approximately 35° C. or more below the melting temperature of a perfectly based-paired double-stranded DNA-RNA hybrid (conveniently written as $T_m - 35°$ C. or more), using such hybridization probes. Further, two HPV RNAs of different types are able to cross-hybridize under non-stringent hybridization conditions, which are defined as approximately 35° C. or more below the melting temperature of a perfectly based-paired double-stranded RNA-RNA hybrid (conveniently written as $T_m - 35°$ C. or more), using such hybridization probes (see Anderson, L. M. et al, *Nucleic Acid Hybridization*, pages 73-111, Eds. B. D. Hames and S. J. Higgins, I.R.L. Press, Oxford, England and Washington, D.C., USA (1985)).

The melting temperatures of DNA-DNA, DNA-RNA and RNA-RNA hybrids of the same nucleotide sequences may be different in various chemical environments. The effect of various compounds on the relative melting temperatures of these various hybrids has been studied for several agents. For example, it is well known that increasing the concentration of formamide differentially destabilizes DNA-DNA hybrids more than DNA-RNA hybrids so that at high concentrations of formamide, such as 80% (v/v), a DNA-RNA hybrid may have a significantly higher melting temperature than a DNA-DNA hybrid of the same nucleotide sequence.

As discussed above, the melting temperature of a DNA-DNA hybrid can be predicted as described in Anderson, L. M. et al, *Nucleic Acid Hybridization*, pages 73-111, Eds. B. D. Hames and S. J. Higgins, I.R.L. Press, Oxford, England and Washington, D.C., USA (1985)). Further, the melting temperature of a DNA-DNA hybrid can be empirically determined as described in Howley, P. et al, *J. Biochem.*, 254: 4876 (1979). The melting temperature of a DNA-RNA hybrid and a RNA-RNA hybrid can also be determined by means well known in the art.

Thus, it is possible to test a tissue sample for the presence of HPV DNA or RNA in general and/or a particular HPV DNA or RNA type by nucleic acid hybridization depending upon what conditions, i.e., stringent or non-stringent, are employed for hybridization.

SUMMARY OF THE INVENTION

Accordingly, an object of the present invention is to ascertain whether cervical cancers and genital lesions, which have the potential to progress to cervical cancer, contain a "new" HPV type(s) and if so, to clone the hypothesized "new"0 HPV type(s).

Another object of the present invention is to provide nucleic acid hybridization probes which are specific for HPV types in general and for the "new" HPV type(s) in particular.

Still another object of the present invention is to provide a method for detecting HPV DNA or RNA in general and the "new" HPV type(s) DNA or RNA in particular, in an unknown sample of DNA or RNA, particularly an unknown sample of DNA or RNA derived from a genital lesion so as to determine the risk of cervical cancer development.

These and other objects of the present invention will be apparent from the detailed description of the invention provided hereinafter.

It has been found in the present invention that the "new" HPV type cloned in the present invention is a novel HPV type, designated HPV 35.

Thus, in one embodiment the above-described objects of the present invention have been met by a recombinant DNA of HPV 35 comprising a cloning vector and substantially all of HPV 35 DNA or fragments thereof.

In other embodiments, the above-described objects of the present invention have been met by essentially pure HPV 35 DNA or fragments thereof or HPV 35 RNA or fragments thereof, or mixtures thereof, and by nucleic acid hybridization probes for HPV DNA or RNA in general and HPV 35 DNA or RNA in particular which comprise the above-described DNAs or RNAs which have been labelled with a detectable marker.

In still another embodiment, the above-described objects of the present invention have been met by a method for detecting HPV DNA or RNA comprising:
(1) carrying out hybridization, under non-stringent conditions, with
  (a) a member selected from the group consisting of
    (i) HPV 35 DNA or fragments thereof labelled with a marker, and
    (ii) HPV 35 RNA or fragments thereof labelled with a marker;
  (b) an unknown sample of DNA or RNA, and
(2) assaying for the presence of cross-hybridization so as to detect HPV DNA or RNA in said sample.

In a further embodiment, the above-described objects of the present invention have been met by a method for detecting HPV 35 DNA or RNA comprising:
(1) carrying out hybridization, under stringent conditions, with
  (a) a member selected from the group consisting of
    (i) HPV 35 DNA or fragments thereof labelled with a marker, and
    (ii) HPV 35 RNA or fragments thereof labelled with a marker;
  (b) an unknown sample of DNA or RNA, and
(2) assaying for the presence of cross-hybridization so as to detect HPV 35 DNA or RNA in said sample.

In a still further embodiment, the above-described objects of the present invention have been met by a method for detecting HPV 35 DNA or RNA comprising:
(1) carrying out hybridization, under stringent conditions, with
  (a) a first fraction of DNA or RNA derived from each genital lesion of a sampling of genital lesions, which sampling shows an epidemiological progression to cervical cancer, and
  (b) a member selected from the group consisting of
    (i) HPV 35 DNA or fragments thereof labelled with a marker, and
    (ii) HPV 35 RNA or fragments thereof labelled with a marker;
(2) carrying out hybridization, under stringent conditions, with
  (a) a second fraction of DNA or RNA derived from each genital lesion of said sampling of genital lesions, and
  (b) an unknown sample of DNA derived from a genital lesion laelled with a marker;
(3) comparing the epidemiological distribution of cross-hybridization obtained in Step (1) with that obtained in Step (2) and the cross-hybridization of the DNA of each lesion which comprises said epidemiological distribution so as to detect HPV 35 DNA or RNA in said sample.

DETAILED DESCRIPTION OF THE INVENTION

Figure 1:
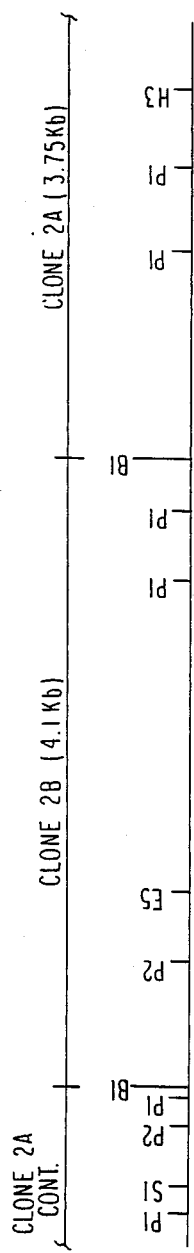
FIG. 1 illustrates the restriction nuclease map of HPV 35 DNA. The following code is used to represent the restriction enzyme sites: B1, BamHI; E5, EcoRV; H3, HindIII; P1, PstI; P2, PvuII; and SI, SphI.

A previously unknown HPV type has been found in the present invention, and designated HPV 35. HPV 35 has been cloned for the first time in the present invention, thus enabling the preparation of nucleic acid hybridization probes for the detection of HPV DNA or RNA in general and HPV 35 DNA or RNA in particular in an unknown sample of DNA or RNA, particularly an unknown sample of DNA or RNA derived from genital lesions.

HPV 35 was isolated and cloned from a cervical adenocarcinoma biopsy obtained in Washington, D.C.

The specific cloning vector employed in the example provided herein to initially clone HPV 35 to prepare HPV 35 clones 1A and 1B was λ L47. Thereafter, the HPV 35 DNA from HPV 35 clones 1A and 1B was subcloned in pBR322 (ATCC No. 37017) to prepare HPV 35 clones 2A and 2B. HPV 35 clones 2A and 2B have been deposited at the American Type Culture Collection under ATCC Nos. 40330 and 40331, respectively.

HPV 35 DNA in its entirety can be excised from HPV 35 clones 2A and 2B using BamHI restriction endonuclease and subcloned in any well known procaryotic and eucaryotic cloning vectors. The particular cloning vector employed for subcloning HPV 35 is not critical and can be any known procaryotic cloning vector such as pUC11, derived vectors such as λ charon or M13 derived bacteriophages (see Maniatis, T. et al, Molecular cloning: a laboratory manual, Cold Spring Harbor Laboratory, Cold Spring Harbor, N.Y. (1982) and Loenen, W.A.M. et al, Gene, 20: 249 (1980)) or any known eucaryotic cloning vector such as pZIP-Neo SV [X1] or pBKTK-1 (see Poueels, P. H. et al, Cloning Vectors: A Laboratory Manual, Elseiver, Amsterdam (1985)).

Fragments of HPV 35 DNA can similarly be excised from HPV 35 clones 2A and 2B using other well known restriction endonucleases and cloned in the above-described cloning vectors. Similarly, the HPV 35 DNA in HPV 35 clones 2A and 2B can be excised therefrom and ligated together and cloned in the above-described cloning vectors to obtain a vector containing substantially all of the HPV 35 genome.

The cloning of HPV 35 DNA or fragments thereof allows for the relatively simple production of large amounts of HPV 35 DNA or fragments thereof for use in the preparation of nucleic acid hybridization probes for HPV DNA or RNA in general and HPV 35 DNA or RNA in particular.

In addition, HPV 35 DNA or fragments thereof can be subcloned in other well known cloning vectors to take advantage of special properties of particular cloning vectors which facilitate the synthesis, in vitro, of RNA homologous to the HPV 35 DNA inserted into the cloning vector (see Maniatis, T. et al, Molecular cloning: A laboratory manual, Cold Spring Harbor Laboratory, Cold Spring Harbor, N.Y. (1982)). Examples of these cloning vectors include pT712 and pT713, each of which is commercially available from GIBCO/BRL, Gaithersburg, MD. HPV 35 DNA or fragments thereof can be subcloned into these cloning vectors so that the HPV 35 DNA or fragments thereof can serve as an efficient template for phage encoded RNA polymerases, e.g., T7, T3 or SP6. Using such cloning vectors and such RNA polymerases, HPV 35 RNA complementary to either one of the strands of HPV 35 DNA or fragments thereof can be synthesized by in vitro transcription using methods well known in the art.

The specific bacterial or eucaryotic hosts for growing the cloning vectors containing HPV 35 DNA or fragments thereof will depend upon the cloning vector employed. For example, a typical host for growing HPV 35 DNA cloned in λ L47 includes *E. coli* NM538 (Frischanf, A. M. et al, *J. Mol. Biol.*, 170: 827 (1983)). Other hosts such as *E. coli* HB101 (Boyer, H. W. et al, *J. Mol. Biol.*, 41: 459 (1969)) can be employed when using pBR322 or pUC11 as the cloning vector. A typical host for growing HPV 35 DNA cloned in pZIP-Neo SV [X1] is Monkey Cos cells while a typical host for growing HPV DNA cloned in pBKTK-1 would be any of a number of well known mammalian cell lines (see Poueels, P. H. et al, Cloning Vectors: A Laboratory Manual, Elseiver, Amsterdam (1985)).

The hybridization of the probes of the present invention to HPV DNA or RNA in general or to HPV 35 DNA or RNA in particular will depend upon the hybridization conditions employed. That is, under non-stringent hybridization conditions, HPV 35 DNA or fragments thereof or HPV 35 RNA or fragments thereof can be employed as hybridization probes for HPV DNA or RNA in general. On the other hand, under stringent hybridization conditions, HPV 35 DNA or fragments thereof or HPV 35 RNA or fragments thereof can be employed as hybridization probes for HPV 35 DNA or RNA in particular.

As discussed above, the DNAs and RNAs of different types of HPV are able to cross-hybridize under non-stringent hybridization conditions, i.e., approximately 35° C. or more below the melting temperature of a perfectly base-paired double-stranded DNA having a base composition equal to that of HPV DNAs or RNAs as a general group.

Furthermore, it is possible to test an unknown sample of DNA or RNA for the presence of a particular HPV type and to identify that type by carrying out hybridization under stringent hybridization conditions, i.e., approximately 10° C. below the melting temperature of a perfectly base-paired double-stranded DNA having a base composition equal to that of HPV DNAs or RNAs as a general group.

In the methods of the present invention, hybridization under non-stringent conditions is carried out by first hybridizing under non-stringent hybridization conditions followed by washing under non-stringent hybridization conditions.

In addition, in the methods of the present invention, hybridization under stringent conditions is carried out by either first hybridizing under non-stringent hybridization conditions followed by washing under stringent hybridization conditions or by first hybridizing under stringent hybridization conditions followed by washing under stringent hybridization conditions. In the first method, i.e., first hybridizing under non-stringent hybridization conditions followed by washing under stringent hybridization conditions, hybrids which form between DNAs or RNAs of different types are unstable but hybrids which form between DNAs and RNAs of the same type are stable.

To determine if an unknown sample of DNA or RNA is of the same or different HPV type as the hybridization probe employed, hybridization is preferably carried out under non-stringent hybridization conditions followed by washing under non-stringent hybridization conditions. After assaying for the presence of hybrids, the detected hybrids are washed under stringent hybridization conditions. In this method, the amount of hybrids which remain after hybridizing under non-stringent hybridization conditions are determined and compared with the amount of hybrids present after washing under stringent hybridization conditions. If the washing under stringent hybridization conditions results in no or minimal reduction in the amount of hybrids formed, then this indicates that the hybrids originally formed, i.e., the ones which formed under non-stringent conditions, were between DNAs or RNAs of the same type. Conversely, abolition of hybrids or a severe reduction of the amount of hybrids which remain after washing under stringent hybridization conditions indicates that the hybrids originally formed, i.e., ones which formed under non-stringent hybridization conditions, were between DNAs or RNAs of different types.

The ability of the HPV DNA or RNA to bind to the unknown sample of DNA or RNA under stringent hybridization conditions is indicative of a high degree of nucleotide sequence homology. On the other hand, the ability of the HPV DNA or RNA to bind to the unknown sample of DNA or RNA only under non-stringent hybridization conditions is indicative of a low or intermediate degree of nucleotide sequence homology. The exact degree of nucleotide sequence homology can only be determined by directly sequencing the unknown DNA and comparing that with the known sequence of the HPV DNA.

In situations in which the detection of HPV DNA or RNA in general in an unknown sample of DNA or RNA, particularly in an unknown sample of DNA or RNA derived from a genital lesion, is being carried out, it is, as a practical matter, advantageous to utilize a hybridization probe composition comprising a mixture of hybridization probes. These hybridization probes comprise probes with sequences representative of all or most of the types suspected of being present in the unknown sample of DNA or RNA. A hybridization probe mixture of DNA or RNA sequences representative of HPV Types 6, 11, 16, 18, 31, 33 and 35 is particularly advantageous when the unknown sample of DNA or RNA is derived from a genital lesion because these HPV types are most likely to be found in genital lesions. Other known HPV types are seldom or never found in genital lesions. For example, HPV Types 1, 2 and 4 are generally found in other types of lesions, i.e., cutaneous warts (see Heilman, C. A. et al, *J. Virol.*, 360:395 (1980)) and thus a hybridization probe mixture of DNA or RNA sequences containing HPV Types 1, 2 and 4 may be advantageous when the unknown sample of DNA or RNA is derived from cutaneous warts but is not as useful when the unknown sample of DNA or RNA is derived from genital lesions.

Examples of sequences of HPV Types 6, 11, 16, 18, 31 and 33 which can be employed in the hybridization probe mixture are described in Gissman, L., *Cancer Surv.*, 3:161 (1984); Pfister, H., *Biochem. Pharmacol.*, 99:111 (1983); Durst, M. et al, *Proc. Natl. Acad. Sci. USA*, 80:3812 (1983); Boshart, M. et al, *EMBO J.*, 3:1151 (1984); Lorincz, A. T. et al *J. Virol.*, 58:225 (1986) and Beaudenon, S., *Nature*, 321:246 (1986). Further, examples of sequences of HPV Types 1, 2 and 4 which can be employed in the hybridization probe mixture are well known in the art (see Heilman, C. A. et al, *J. Virol.*, 360:395 (1980)). Thus, with the disclosure herein as to HPV 35 and with the knowledge of one skilled in the art as to HPV Types, 6, 11, 16, 18, 31 and 33 and to other HPV types such as HPV Types 1, 2 and 4, hybridization probe mixtures can be readily prepared.

In the hybridization probe mixtures, the particular percentage of DNAs or RNAs of each HPV type is not critical in the present invention. Generally, roughly equal molar amounts of DNAs or RNAs of each HPV type are employed in the mixture.

Nucleic acid hybridization as a means of detecting and typing HPV can be carried out in solution as described above (see Loggins, J. R. et al, *Cancer Res.*, 39:545 (1979)) or on a solid support (see Maniatis, T. et al, Molecular cloning: a laboratory manual, Cold Spring Harbor Laboratory, Cold Spring Harbor, New York (1982) or in situ (see Brigati, D. J. et al, *Virol.*, 126:32 (1983) and Beckmann, A. M. et al, *J. Med. Virol.*, 16:265 (1985)).

Hybridization on a solid support can be carried out using a number of different procedures. One such procedure involves purifying all of the unknown DNAs or RNAs, immobilizing such to a solid support in single-stranded form, followed by hybridization with labelled HPV 35 DNA or fragments thereof or labelled HPV 35 RNA or fragments thereof.

Alternatively, the purified unknown DNAs can be digested with one or more restriction endonucleases and the resulting DNA fragments in the samples can be separated electrophoretically. The DNA fragments can then be transferred to a solid support and hybridized with labelled HPV 35 DNA or fragments thereof or labelled HPV 35 RNA or fragments thereof.

Hybridization in situ is performed on glass slides and the end result of the procedure is viewed through a microscope. In this procedure, the DNA or RNA is not purified from the cells but is left with all of the other cellular components.

HPV 35 RNA or fragments thereof are preferably used as nucleic acid hybridization probes for HPV DNA in general and HPV 35 DNA in particular when using crude extracts, particularly crude genital lesion extracts rather than purified DNA, e.g., from such genital lesions.

When employing HPV 35 RNA as a hybridization probe for detecting HPV 35 DNA in an unknown sample of DNA, it is preferable that the DNA-RNA hybrids formed after first hybridizing under stringent hybridization conditions, are treated with pancreatic RNaseA (about 20 mg/ml in 50 mM NaCl (pH 7.0)) at room temperature, followed by washing under stringent hybridization conditions.

The HPV 35 DNA or fragements thereof or HPV 35 RNA or fragments thereof are useful as nucleic acid hybridization probes for HPV DNA or RNA in general and HPV 35 DNA or RNA in particular when labelled with a radioactive marker such as $^{32}P$, $^{14}C$, $^{3}H$, $^{125}I$ or $^{35}S$.

HPV 35 DNA or fragments thereof can be radioactively labelled, for example, by "nick-translation" by well known means, as described in, for example, Rigby, P. J. W. et al, *J. Mol. Biol.*, 113:237 (1977) and by T4 DNA polymerase replacement synthesis as described in, for example, Deen, K. C. et al, *Anal. Biochem.*, 135:456 (1983)).

HPV 35 RNA or fragments thereof can be labelled with a radioactive marker by in vitro transcription as described in, for example, Davanloo, P. et al, *Proc. Natl. Acad. Sci., USA* 81:2035 (1984)). Since RNA polymerases can utilize labelled precursors, it is possible to synthesize labelled RNA by this method so as to prepare HPV 35 RNA probes for the detection of HPV DNA or RNA in general or HPV 35 DNA or RNA in particular. The labelled precursors which can be used to synthesize labelled RNA include precursors containing radioactive markers such as $^{32}P$, $^{14}C$, $^{3}H$, $^{125}I$ or $^{35}S$.

HPV 35 DNA or fragments thereof or HPV 35 RNA or fragments thereof are also useful as nucleic acid hybridization probes for HPV DNA or RNA in general and HPV 35 DNA or RNA in particular when labelled with a non-radioactive marker such as biotin, an enzyme or fluorescent group. Biotin acts as a hapten-like group and can be bound to the DNA or RNA and detected by binding an avidin-conjugated enzyme or streptavidin-conjugated enzyme to the biotin followed by washing to remove non-specifically bound enzyme. Upon addition of appropriate substrates for the enzyme, the conversion of the substrate to a colored product can be detected (see Leary, J. J. et al, *Proc. Acad. Sci., USA*, 80:4045 (1983)). Examples of such enzymes include alkaline phosphatase and horseradish peroxidase. In addition, fluorescent molecules such as fluorescein and rhodamine can be chemically conjugated to avidin or streptavidin and employed as the non-radioactive marker.

Alternatively, the above-described enzymes or fluorescent molecules can be chemically conjugated directly to the HPV 35 DNA or fragments thereof or HPV 35 RNA or fragments thereof as described in, for example, Renz, M, *EMBO J.*, 6:817 (1983), and used in this manner as hybridization probes.

The thus labelled HPV 35 DNA or HPV 35 RNA or fragments thereof can be used as described above in hybridization studies with an unknown sample of DNA or RNA, particularly an unknown sample of DNA or RNA derived from a genital lesion, to determine if the sample contains HPV DNA or RNA in general and HPV 35 DNA in particular.

The unknown sample of DNA, in addition to being derived from a genital lesion, can be derived from other lesions such as throat, oral or skin lesions.

The unknown sample of DNA or RNA can be obtained by, for example, biopsying an epithelial lesion, scraping the cervix or swabbing the cervix to obtain exfoliated cells. In addition, the unknown sample of DNA or RNA can be obtained from bacterial cells in which DNA from a lesion has been cloned using well known means as described in Maniatis, T. et al, Molecular cloning: A laboratory manual, Cold Spring Harbor Laboratory, Cold Spring Harbor, New York (1982) and Gissman, L., *Cancer Surv.*, 3:161-181 (1984).

In the methods of the present invention, assaying for cross-hybridization can be carried out by assaying for the presence of the radioactive or non-radioactive marker associated with double-stranded nucleic acid hybrids. The methods for determining whether a specific marker is present will depend upon the marker employed and are well known in the art.

In the embodiment of the present invention wherein the detection of HPV 35 DNA or RNA is based upon a comparison of the epidemiological distribution of cross-hybridization of an unknown sample of DNA or RNA derived from a genital lesion with that of HPV 35 DNA, the unknown sample of DNA or RNA may exhibit less than 50% cross-hybridization with HPV 35 DNA under moderately stringent hybridization conditions, i.e., using hydroxyapatite chromatography for determining whether two HPVs represent different isolates of a common type or represent isolates of a different type, yet, may still be considered HPV 35 DNA or RNA by the definitions herein. As a result, it is necessary to also compare the cross-hybridization of each lesion which comprises the epidemiological distribution in order to detect HPV 35 DNA or RNA in the sample. This is because it may be possible for different HPV types to show the same or similar epidemiological distributions. However, by demonstrating that the same lesions which comprise the epidemiological distribution cross-hybridize both to HPV 35 DNA and the unknown sample of DNA or RNA derived from a genital lesion it is possible to definitively conclude that the sample of unknown DNA or RNA derived from a genital lesion is HPV 35 DNA or RNA.

As discussed in more detail below, HPV 35 DNA or RNA has been found to be present in approximately 1% to 4% of cervical lesions from mild dysplasias to invasive cancer. Thus, HPV 35 DNA or RNA is rather uniformly distributed in cervical lesions of various grades. On the other hand, other HPV types, such as HPV Types 6, 11, 16, 18 and 31 exhibit a different distribution in cervical lesions of various grades. Thus, in the embodiment of the present invention wherein the detection of HPV 35 DNA or RNA is based upon a comparison of the epidemiological distribution of cross-hybridization of an unknown sample of DNA or RNA derived from a genital lesion with that of HPV 35 DNA, the unknown sample of DNA or RNA derived from a genital lesion would cross-hybridize with cervical lesions. If such an epidemiological distribution of cross-hybridization is found with the unknown sample of DNA or RNA derived from a genital lesion, then this unknown sample of DNA or RNA may be HPV 35 DNA or RNA. By demonstrating that the same lesions which comprise the epidemiological distribution also cross-hybridize with the unknown sample of DNA or RNA derived from a genital lesion, it can be concluded that the unknown sample of DNA or RNA derived from a genital lesion is HPV 35 DNA or RNA.

The particular size of the HPV 35 DNA or HPV 35 RNA fragments which can be employed as hybridization probes in the present invention is not critical. The size of the HPV 35 DNA or HPV 35 RNA fragments can be, for example, from about 15 to about 8000 bases or base pairs, depending on whether single stranded or double stranded probes are employed, preferably about 300 to about 800 bases or base pairs. When carrying out hybridization in situ, it is preferable that the size of the HPV 35 DNA or HPV 35 RNA fragments is smaller than about 500 bases or base pairs since fragments of this size hybridize in situ more efficiently than HPV DNA or HPV RNA fragments larger than about 1000 bases or base pairs. When using double-stranded DNA or RNA, the DNA or RNA must be denatured prior to carrying out hybridization.

The HPV 35 DNA fragments can be obtained by restriction endonuclease digestion of the HPV 35 clones 2A and 2B or by synthetically manufacturing such using any of the commercially available DNA synthesizing apparatus or by well known chemical methods using the HPV 35 DNA sequence which can be determined by well known means (Sanger, S. et al, *Proc. Natl. Acad. Sci. USA*, 74:5363 (1977)).

When detecting HPV 35 DNA or RNA, it is preferable to use substantially all of the HPV 35 genome as a hybridization probe.

The following example is given to further illustrate the present invention and is no way intended to limit the scope of the present invention. Unless otherwise indicated, all parts, percents, ratios and the like are by weight.

EXAMPLE (A) Cloning of HPV 35 DNA

The starting material employed was a cervical adenocarcinoma biopsy obtained from Washington, D.C. consisting of a few milligrams of tissue. Total DNA was purified as described in (Maniatis, T. et al, Molecular cloning: A laboratory manual, Cold Spring Harbor Laboratory, Cold Spring Harbor, New York (1982)). More specifically, the tissue was minced, then digested in 1.0 ml of 50 mM Tris-HCl, pH 8.0 containing 0.6% (w/v) sodium dodecyl sulfate and 50 µg/ml proteinase K at 37° C. overnight. The resulting digest was extracted twice with 1.0 ml of phenol:chloroform (1.1 (v/v)). DNA was then precipitated from the aqueous phase by addition of 2 volumes of 90% (v/v) ethanol. The precipitated DNA was redissolved in 10 mM Tris, 1.0 mM EDTA buffer, pH 8.0 (hereinafter "TE buffer") at a concentration of about 1.0 mg/ml.

The DNA was digested to completion with PstI, electrophoresed in 1% (w/v) agarose gels and DNA transferred to nitrocellulose filters as described in Southern, E. M., *J. Mol. Biol.*, 98:503 (1975). The filters were then probed under non-stringent hybridization conditions ($T_m - 35°$ C.) and stringent hybridization conditions ($T_m - 10°$ C.) with DNA from HPV types 6, 11, 16, 18 and 31. Hybridization was performed overnight at 43° C. in 1.0 M NaCl, 50 mM sodium phosphate buffer (pH 7.4), 1.0 mM EDTA, 2% (w/v) sodium dodecyl sulfate, 0.1% (w/v) gelatin, 50 µg/ml tRNA and 30% (v/v) formamide. Four 30 minute washes were performed at 55° C. in 1.2× SSC (1× SSC is 0.15 M NaCl plus 0.015 M sodium citrate), 10 mM sodium phosphate (pH 7.4), 1.0 mM EDTA and 0.5% (w/v) sodium dodecyl sulfate. Hybridization was achieved under non-stringent conditions with HPV types 6, 11, 16, 18 and 31 but not under stringent hybridization conditions.

The resulting purified DNA and λ L47 were digested with BamHI restriction endonuclease, which produced fragments of 3.75 kb and 4.1 kb, the sum of which, i.e., 7.85 kb, is the typical size for a papillomavirus genome. Each of these fragments was cloned into the single BamHI site of λ L47. More specifically, 2.0 µg of the resulting purified DNA, and 2.0 µg of λ L47 DNA were cut with 10 units of BamHI in a total volume of 50 µl of TE buffer for 1 hr at 37° C. The resulting reaction mixture was then diluted with 400 μl of TE buffer and phenol extracted with an equal volume of phenol:chloroform as described above. The aqueous phase was then extracted with chloroform:isoamyl alcohol (24:1 (v/v)) and DNA from the aqueous phase was precipitated with 80% (v/v) ethanol and dried. The dried DNA was then suspended in 10 μl of 1 × ligase buffer comprising 66 mM Tris-HCl, 6.6 mM MgCl$_2$, 10 mM DTT and 0.1 mM ATP and incubated at 42° C. for 2 hours to allow the λ arms to anneal. Next, 0.5 μl of T4 DNA ligase, i.e., about 1 unit, and 0.5 μl of 10 mM ATP, pH 7.0 was added to the reaction solution and ligation was allowed to proceed at 12° C. overnight.

Next, the ligation products were packaged to form infectious phage and used to infect E. col. NM538. More specifically, a single colony of E. coli NM538 growing on an agarose plate comprising 10 g Tryptone and 5.0 g NaCl per liter (hereinafter "TN medium") was selected and grown overnight at 37° C. in 20 ml of TN medium on a shaking platform (250 rpm) to early stationary phase. The cell culture was then diluted four fold with TN medium and grown for 3 hours. Next, the cells were harvested by centrifuging for 5 minutes at 5,000 rpm in a Sorvall HB-4 rotor and the resulting cell pellet was resuspended in 0.25 of the original volume, in 10 mM MgSO$_4$ and stored at 4° C.

The packaged infectious phages were prepared using a commercially available BRL Lambda In Vitro Packaging System (see Maniatis, T. et al, Molecular cloning: A laboratory manual, Cold Spring Harbor Laboratory, Cold Spring Harbor, N.Y. (1982).

100 μl of an appropriate dilution of packaged phage in phase storage buffer comprising 0.5 M Tris-HCl (pH 8.0), 0.1 M NaCl, 0.01 M MgSO$_4$ and 0.01% (w/v) gelatin (Difco) to give 1.5×10$^4$ plaques per 9 cm diameter plates, was added to 100 μl of E. coli NM538 prepared as described above in a 10–15 ml test tube, gently mixed and incubated at room temperature for 15 minutes. Then, the cell-phage solution was plated on Trypticase soy broth agar plates comprising 10 g of Trypticase soy broth, 5.0 g NaCl and 15 g agar per liter, which had been prepared at least one day in advance and which had been pre-warmed at 37° C. Thereafter, 3–5 ml of an agarose overlayer comprising 0.5% agarose (ultrapure, electrophoresis grade) dissolved in 10 mM MgSO$_4$, which had been heated in a microwave oven until the solution boiled and then cooled to 45° C. before use, was placed over the plated cells-phage. After the agarose had solidified, the plates were transferred to a 37° C. forced air incubator with good circulation with the lids of the plates cracked for 30 minutes and then the lids were closed and the plates inverted. After 8–12 hours, plaques became apparent.

Infection resulted in confluent lysis of bacteria on the plates. Recombinant phage carrying HPV DNA were localized by performing "plaque lifts" as described by Benton, W. D. et al, Science, 196:180 (1977). More specifically, confluent lysed plates were placed at 4° C. for 1 hour to harden the agarose. Then, an appropriately sized piece of nitrocellulose filter was placed onto each plate by bowing it in the middle, touching the center of the plate and working the contact points toward the edge. Then, four assymetric holes were punched through the nitrocellulose filter and the agar with a small gauge needle and the positions of the holes were marked on the bottom of the plate with a permanent marker. This allowed the nitrocellulose filter and any other areas containing positive signals to be referenced to corresponding positions on the plates. After 10 minutes, the nitrocellulose filters removed and the DNA was denatured by placing the nitrocellulose filters, plaque side facing upwards, into a dish containing 200 ml of 0.5 M NaOH, 2.0 M NaCl for 1 minute. The nitrocellulose filters were then neutralized by immersion in 500 ml of 0.5 M Tris-HCl, 2.0 M NaCl, pH 7.5 for 5 minutes. Next, the filters were rinsed in 6× SSC comprising 0.9 M NaCl, 0.09 M sodium citrate for 1 minute, dried on Whatman 3 MM paper and then baked for 30 minutes at 80° C. under vacuum.

Thereafter, non-stringent hybridization using HPV 16 DNA labelled with $^{32}$P by "nick translation" as a probe was carried out on the DNA isolated from the lifted plaques (see Rigby, P. J. W. et al, J. Mol. Biol., 113:237 (1977) and Maniatis, T. et al, Molecular cloning: A laboratory manual, Cold Spring Harbor Laboratory, Cold Spring Harbor, N.Y. (1982)) followed by washing and autoradiography. More specifically, hybridization was performed at 41° C. in a solution comprising 1.0 M NaCl, 28% (v/v) formamide, 50 mM N-Tris (hydroxymethyl)-methyl-2-aminoethane sulfonic acid (hereinafter "TES"), 10× Denhardt solution, 0.1 mM EDTA and 10 mM sodium phosphate (pH 7.4). Then a non-stringent wash was carried out at 52° C. using 1.1× SSC (comprising 0.165 M NaCl and 0.0165 M sodium citrate) in 10 mM sodium phosphate (pH 7.4), 0.1 mM EDTA.

By correspondence with the sites of radioactive exposure, a region of the plate containing phage, which contained DNA that hybridized to HPV 16 DNA, was excised and used to reinfect E. coli NM538 as described above. Localization of phage plaques containing HPV DNA was accomplished by repeating the above procedure. Seven plaques were identified from among the 2×10$^5$ plaques screened and three types of clones were found. Two clones exhibited a 3.75 kb insert, two clones a 4.1 kb insert and two clones a 4.3 kb insert. All similar size clones had identical restriction maps. The 3.75 kb and 4.1 kb clones did not cross-hybridize. However, the 4.3 kb clones were found to be homologues to the 3.75 kb clones and also to human genomic DNA. This suggests that these clones contained junction fragments between human DNA and integrated copies of HPV 35 DNA and thus were not analyzed further. A clone containing the 3.75 kb fragment was designated HPV 35 clone 1A and a clone containing the 4.1 kb fragment was designated HPV 35 clone 1B.

The HPV DNA of HPV 35 clones 1A and 1B were then digested with BamHI and subcloned in the single BamHI site of pBR322. The resulting recombinant DNA was designated HPV 35 clones 2A and 2B. HPV 35 clones 2A and 2B have been deposited at the American Type Culture Collection under ATCC No. 40330 and ATCC No. 40331, respectively.

(B) Characterization of HPV 35 DNA 1. Hybridization Studies

Hybridization studies were carried out on HPV 35 clones 2A and 2B DNA to demonstrate that HPV 35 clones 2A and 2B were a new HPV type.

More specifically, $^{32}$P "nick translated" DNA prepared from HPV 35 clones 2A and 2B were hybridized by Southern blotting under stringent conditions to 5 ng of DNA from HPV Types 1 to 34. DNA from HPV Types 1 to 34 were obtained from Dr. Gerard Orth of the Institut Pasteur, Paris, France, the assignor of HPV type designations, and Dr. Ethel-Michelle de Villiers of the Papilloma Reference Center in Heidelberg, West Germany, in pre-immobilized form on nitrocellulose filters. More specifically, hybridization was performed at 41° C. in a solution comprising 1.0 M NaCl, 28% (v/v) formamide, 50 mM N-Tris TES, 10× Denhardt solution, 0.5 mM EDTA and 20 mM sodium phosphate (pH 7.4). Then, a stringent wash was carried out at 65° C. using 0.03× SSC (comprising 0.0045 M NaCl and 0.00045 M sodium citrate) in 10 mM sodium phosphate (pH 7.4), 0.1 mM EDTA.

While significant homology was detected between the recombinant DNA of HPV 35 clones 2A and 2B and HPV types 2, 3, 6, 7, 8, 10, 11, 13, 16, 18, 30 and 31 under non-stringent hybridization conditions, no homology was observed with any of HPV types 1–34 under stringent hybridization conditions, thus demonstrating that HPV 35 clones 2A and 2B represent a new HPV type.

2. Restriction Endonuclease Map

Figure 2:
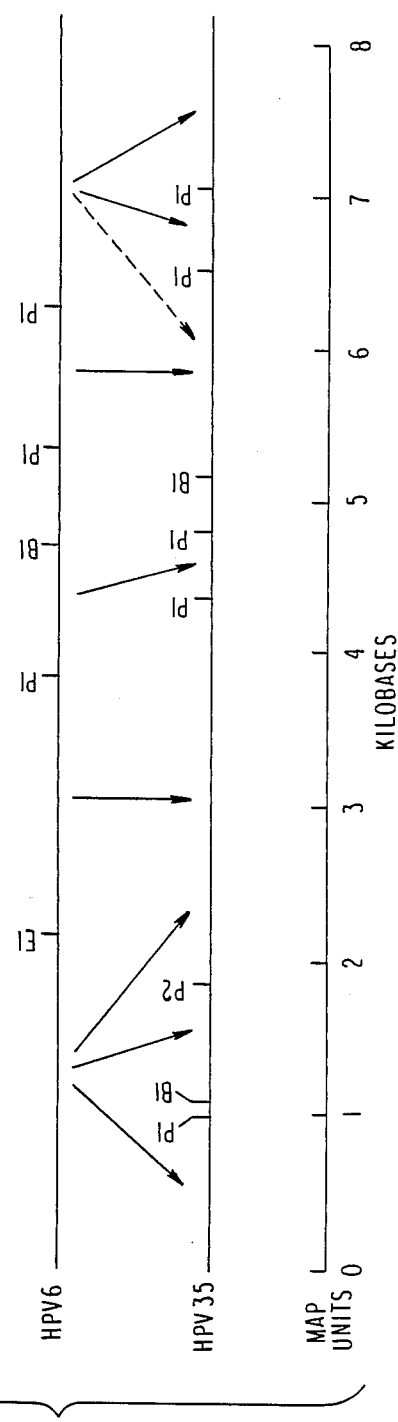
FIG. 2 shows regions of partial homology between HPV 6 and HPV 35 DNA as determined by nucleic acid hybridization under non-stringent hybridization conditions. The arrows connect regions which exhibit homology. The dotted arrow indicates a region which has only weak homology. The smallest BamHI to PstI fragment of HPV 6 did not hybridize to HPV 35. Each of the maps in FIG. 2 is arranged so that the ends of the linear map correspond to the relative position of the HpaI site of HPV 6. The positions of the open reading frames deduced from HPV 6 are shown above the homology map.

The restriction endonuclease map for HPV 35 is shown in FIG. 2. The following restriction enzymes do not cut HPV 35 DNA: SalI, XbaI, NcoI and HpaI.

3. Genomic Organization

In order to demonstrate that the genome of HPV 35 had the same or similar open reading frame organization to HPV 6, the following hybridization studies were carried out. Purified DNA from HPV 35 clones 2A and 2B was subjected to Southern blotting using $^{32}$P "nick translated" fragments of HPV 6 DNA as a probe under non-stringent conditions and under stringent conditions as described above. More specifically, fragments of the BamHI-linearized HPV 6b clone were generated with EcoRI and PstI, then gel purified, nick translated with $^{32}$P and used to probe Southern blots containing: (a) PstI restriction digests of the purified BamHI fragments of HPV 35 clone 2A DNA or (b) PvuII-PstI restriction digests of the purified BamHI fragments of HPV 35 clone 2B DNA. The results, which are shown in FIG. 1, demonstrate that the DNA of HPV 35 clones 2A and 2B have the same genomic organizations as HPV 6.

4. Epidemiological Distribution

In order to demonstrate that hybridization probes prepared from HPV 35 clones 2A and 2B hybridize efficiently under stringent conditions only to HPV 35 DNA, and that these hybridization probes can be used to detect genital lesions which contain HPV 35 and to distinguish such genital lesions from genital lesions which contain the DNA of other HPV types, e.g., 6, 11, 16, 18, 31 or 33, the DNA of a collection of cervical biopsies and cervical swabs containing exfoliated cells from the Washington, D.C. metropolitan area (including Maryland and Virginia) and Michigan and surrounding states, were analyzed by nucleic acid hybridization under stringent and non-stringent conditions, for the presence of specific HPV DNAs using probes specific for various HPV types, including probes specific for HPV 35. The biopsies were bisected with half of the specimens being processed for conventional light microscopy and the other half being frozen and stored at −20° C. for molecular analysis. The tissues on which Southern blot hybridizations were performed were sectioned on a cryostat in order to obtain material for DNA extraction. Approximately every fifteenth section was stained with hematoxylin and eosin stain and examined microscopically in order to confirm that this tissue sample was comparable to the portion of the specimen analyzed by light microscopy. Exfoliated cervical cells were analyzed by standard cytological methods, e.g., pap smear, on paired samples, the other of which was used for DNA analysis.

High molecular weight DNA was prepared from the samples as described above. 1 to 10 μg of purified cellular DNA were digested with either PstI or BamHI and the digested samples were electrophoresed in 1.0% (w/v) agarose gels and transferred to nitrocellulose filters. Thereafter, hybridization was carried out under stringent conditions as described above with nick-translated $^{32}$P-labelled HPV DNAs from the types discussed above. (For HPV 35 DNA, a mixture of HPV DNA from HPV 35 clones 2A and 2B was employed.) Note, since the HPV DNAs were propagated in pBR322 or related vectors, in order to minimize the possibility of reactivity with pBR322 and related vector-like sequences in the tissue samples, all probes were electrophoretically purified to remove most of the associated vector sequences. Additional hybridization was also carried out in the presence of labelled pBR322 and related vectors, to reveal any potential false positives due to the plasmid-like sequences in the tissue samples. The results are shown in Table 1 below. The results in Table 1 are graphically illustrated in FIG. 3.

TABLE 1

Distribution of HPV Types in Cervical Biopsies from the Washington, D.C. Metropolitan Area and Michigan

|  | Normal Squamous Epithelium[a] | Metaplastic Squamous Epithelium[b] | Condyloma | CIN I | CIN II | CIN III | Squamous Carcinoma | Endocervical Adenocarcinoma |
|---|---|---|---|---|---|---|---|---|
| HPV 6 | 5 (1.14%) | 1 (1.82%) | 17 (29.31%) | 6 (11.11%) | 9 (16.36%) | 1 (3.57%) | 0 | 0 |
| HPV 11 | 0 | 1 (1.82%) | 7 (12.07%) | 2 (3.70%) | 0 | 0 | 0 | 0 |
| HPV 16 | 10 (2.28%) | 1 (1.82%) | 4 (6.89%) | 11 (20.37%) | 22 (40.0%) | 19 (67.86%) | 19 (38.78%) | 2 (28.57%) |
| HPV 18 | 0 | 1 (1.82%) | 1 (1.72%) | 1 (1.85%) | 1 (1.82%) | 2 (7.14%) | 12 (24.40%) | 2 (28.57%) |
| HPV 31 | 4 (0.91%) | 0 | 1 (1.72%) | 8 (14.81%) | 7 (12.73%) | 3 (10.71%) | 3 (6.12%) | 0 |
| HPV 33 | 3 (0.68%) | 1 (1.82%) | 0 | 3 (5.56%) | 1 (1.82%) | 0 | 1 (2.04%) | 0 |
| HPV 35 | 5 (1.14%) | 1 (1.82%) | 1 (1.72%) | 2 (3.70%) | 1 (1.82%) | 0 | 1 (2.04%) | 1 (14.29%) |
| Total No. of HPV Positive Biopsies | 27 | 6 | 31 | 33 | 41 | 25 | 36 | 5 |
| Total No. of HPV Negative Biopsies | 412 | 49 | 27 | 21 | 14 | 3 | 13 | 2 |
| Total No. |  |  |  |  |  |  |  |  |

TABLE 1-continued

| Distribution of HPV Types in Cervical Biopsies from the Washington, D.C. Metropolitan Area and Michigan | | | | | | | |
|---|---|---|---|---|---|---|---|
| | Normal Squamous Epithelium[a] | Metaplastic Squamous Epithelium[b] | Condyloma | CIN I | CIN II | CIN III | Squamous Carcinoma | Endocervical Adenocarcinoma |
| of Biopsies | 439 | 55 | 58 | 54 | 55 | 28 | 49 | 7 |

[a]These biopsies were from the portio of the cervix.
[b]These biopsies were from the transformation zone.

Figure 3:
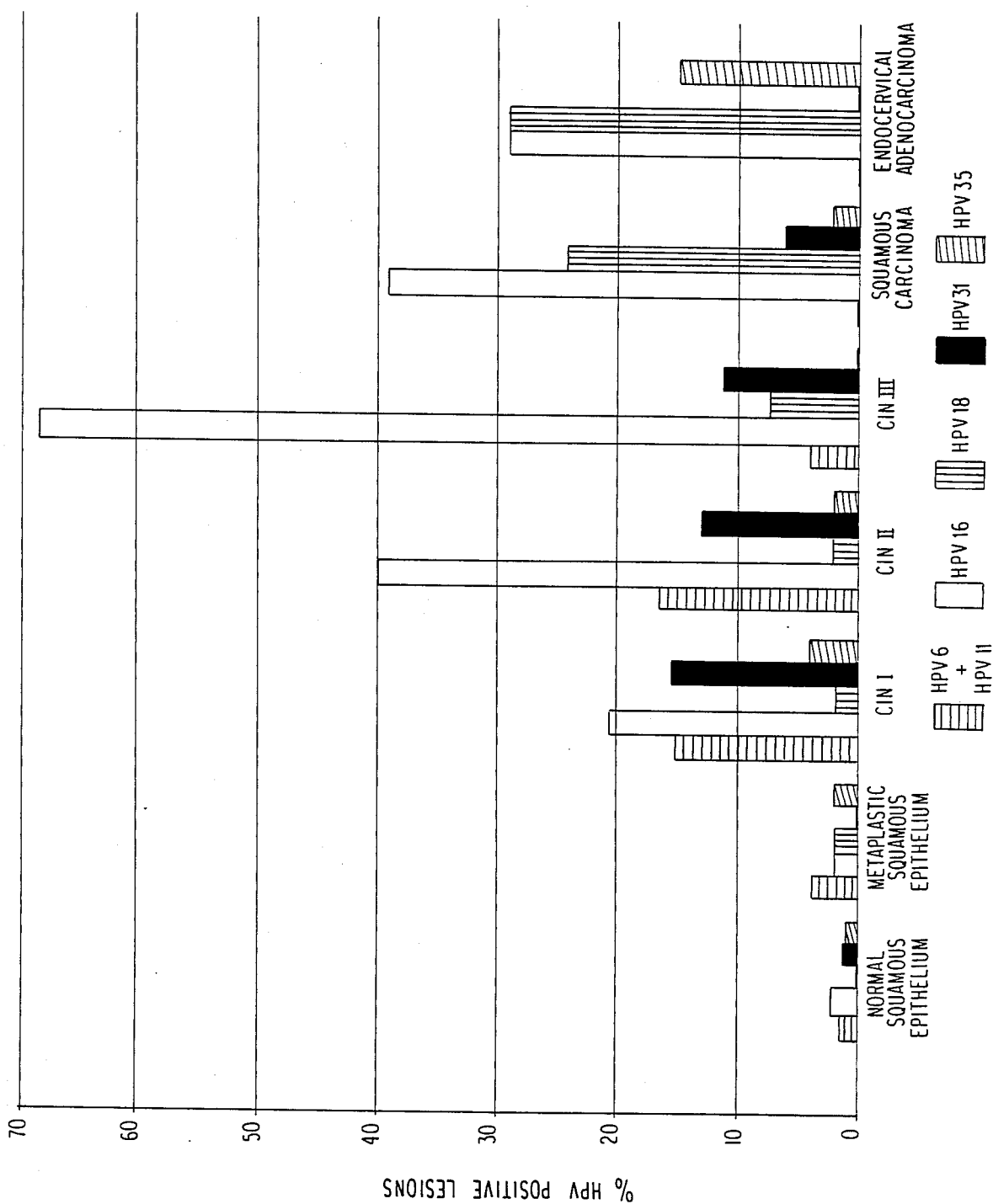
FIG. 3 graphically illustrates the distribution of HPV types in various lesions based on the data in Table 1.

Table 1 and FIG. 3 demonstrate that cervical biopsies containing HPV 35 can be distinguished from biopsies containing other HPV types, e.g., 6, 11, 16, 18, 31 or 33, not only by the criteria of degree of cross-hybridization in solution followed by hydroxyapatite chromatography but, also by the ability of an HPV 35 DNA probe to specifically detect and identify distinct populations of genital lesions, i.e., ones which contain HPV 35 DNA, as compared to ones which contain other HPV types. In addition, the results in Table 1 and FIG. 3 show that the epidemiological distribution of HPV 35 DNA among cervical biopsies is distinct from that found for some other HPV types.

While this invention has been described in detail and with reference to specific embodiments thereof, it will be apparent to one skilled in the art that various changes and modifications could be made therein without departing from the spirit and scope thereof.

I claim:

1. A recombinant DNA of HPV 35 comprising a cloning vector and substantially all of HPV 35 DNA or fragments thereof.

2. The recombinant DNA of HPV 35 as claimed in claim 1, wherein said cloning vector is selected from the group consisting of pBR322, pUC11, λ charon, λ L47, M13 derived bacteriophage, pZIP-Neo SV [X1], pBKTK-1, pT712 and pT713.

3. The recombinant DNA of HPV 35 as claimed in claim 1, wherein said fragments are about 15 to about 8000 base pairs in size.

4. The recombinant DNA of HPV 35 as claimed in claim 3, wherein said fragments are about 300 to about 800 base pairs in size.

5. The recombinant DNA of HPV 35 as claimed in claim 1, wherein said recombinant DNA has the identifying characteristics of HPV 35 clones 2A and 2B (ATCC No. 40330 and ATCC No. 40331, respectively).

6. The recombinant DNA of HPV 35 as claimed in claim 1, wherein the HPV DNA of said recombinant DNA is labelled with a marker.

7. The recombinant DNA of HPV 35 as claimed in claim 6, wherein said marker is a radioactive marker.

8. The recombinant DNA of HPV 35 as claimed in claim 7, wherein said marker is a radioactive marker selected from the group consisting of $^{32}P$, $^{14}C$, $^{3}H$, $^{125}I$ and $^{35}S$.

9. The recombinant DNA of HPV 35 as claimed in claim 6, wherein said marker is a non-radioactive marker selected from the group consisting of biotin, an enzyme and a fluorescent molecule.

10. The recombinant DNA of HPV 35 as claimed in claim 9, wherein said enzyme is selected from the group consisting of alkaline phosphatase and horseradish peroxidase.

11. The recombinant DNA of HPV 35 as claimed in claim 9, wherein said fluorescent molecule is selected from the group consisting of fluorescein and rhodamine.

12. Essentially pure HPV 35 DNA or fragments thereof.

13. The essentially pure HPV 35 DNA as claimed in claim 12, wherein said HPV 35 DNA or fragments thereof are produced biologically.

14. The essentially pure HPV 35 DNA as claimed in claim 12, wherein said HPV 35 DNA or fragments thereof are produced chemically.

15. The essentially pure HPV 35 DNA as claimed in claim 12, wherein said fragments are about 15 to about 8000 bases or base pairs in size.

16. The essentially pure HPV 35 DNA as claimed in claim 15, wherein said fragments are about 300 to about 800 bases or base pairs in size.

17. The essentially pure HPV 35 DNA as claimed in claim 12, wherein said HPV 35 DNA or fragments thereof are labelled with a marker.

18. The essentially pure HPV 35 DNA as claimed in claim 17, wherein said marker is a radioactive marker.

19. The essentially pure HPV 35 DNA as claimed in claim 18, wherein said marker is a radioactive marker selected from the group consisting of $^{32}P$, $^{14}C$, $^{3}H$, $^{125}I$ and $^{35}S$.

20. The essentially pure HPV 35 DNA as claimed in claim 17, wherein said marker is a non-radioactive marker selected from the group consisting of biotin, an enzyme and a fluorescent molecule.

21. The essentially pure HPV 35 DNA as claimed in claim 20, wherein said enzyme is selected from the group consisting of alkaline phosphatase and horseradish peroxidase.

22. The essentially pure HPV 35 DNA as claimed in claim 20, wherein said fluorescent molecule is selected from the group consisting of fluorescein and rhodamine.

23. Essentially pure HPV 35 RNA or fragments thereof.

24. The essentially pure HPV 35 RNA as claimed in claim 23, wherein said HPV 35 RNA or fragments thereof are produced biologically.

25. The essentially pure HPV 35 RNA as claimed in claim 23, wherein said HPV 35 RNA or fragments thereof are produced chemically.

26. The essentially pure HPV 35 RNA as claimed in claim 23, wherein said fragments are about 15 to about 8000 bases or base pairs in size.

27. The essentially pure HPV 35 RNA as claimed in claim 26, wherein said fragments are about 300 to about 800 bases or base pairs in size.

28. The essentially pure HPV 35 RNA as claimed in claim 23, wherein said HPV 35 RNA or fragments thereof are labelled with a marker.

29. The essentially pure HPV 35 RNA as claimed in claim 28, wherein said marker is a radioactive marker.

30. The essentially pure HPV 35 RNA as claimed in claim 29, wherein said marker is a radioactive marker selected from the group consisting of $^{32}P$, $^{14}C$, $^{3}H$, $^{125}I$ and $^{35}S$.

31. The essentially pure HPV 35 RNA as claimed in claim 28, wherein said marker is a non-radioactive marker selected from the group consisting of biotin, an enzyme and a fluorescent molecule.

32. The essentially pure HPV 35 RNA as claimed in claim 31, wherein said enzyme is selected from the group consisting of alkaline phosphatase and horseradish peroxidase.

33. The essentially pure HPV 35 RNA as claimed in claim 31, wherein said fluorescent molecule is selected from the group consisting of fluorescein and rhodamine.

34. An HPV 35 hybridization probe comprising a member selected from the group consisting of (i) HPV 35 DNA or fragments thereof labelled with a marker and (ii) HPV 35 RNA or fragments thereof labelled with a marker.

35. The HPV 35 hybridization probe as claimed in claim 34, wherein said fragments are about 15 to about 8000 bases or base pairs in size.

36. The HPV 35 hybridization probe as claimed in claim 35, wherein said fragments are about 300 to about 800 bases or base pairs in size.

37. The HPV 35 hybridization probe as claimed in claim 34, wherein said marker is a radioactive marker.

38. The HPV 35 hybridization probe as claimed in claim 37, wherein said marker is a radioactive marker selected from the group consisting of $^{32}P$, $^{14}C$, $^{3}H$, $^{125}I$ and $^{35}S$.

39. The HPV 35 hybridization probe as claimed in claim 34, wherein said marker is a non-radioactive marker selected from the group consisting of biotin, an enzyme and a fluorescent molecule.

40. The HPV 35 hybridization probe as claimed in claim 39, wherein said enzyme is selected from the group consisting of alkaline phosphatase and horseradish peroxidase.

41. The HPV 35 hybridization probe as claimed in claim 39, wherein said fluorescent molecule is selected from the group consisting of fluorescein and rhodamine.

42. An HPV 35 hybridization probe composition comprising (a) a member selected from the group consisting of (i) HPV 35 DNA or fragments thereof labelled with a marker and (ii) HPV 35 RNA or fragments thereof labelled with a marker and, (b) DNA or RNA or fragments thereof of at least one other HPV type labelled with a marker.

43. The HPV hybridization probe composition as claimed in claim 42, wherein at least any one of said fragments are about 15 to about 8000 bases or base pairs in size.

44. The HPV hybridization probe composition as claimed in claim 43, wherein at least any one of said fragments are about 300 to about 800 bases or base pairs in size.

45. The HPV hybridization probe composition as claimed in claim 42, wherein at least any one of said marker is a radioactive marker.

46. The HPV hybridization probe composition as claimed in claim 45, wherein at least any one of said marker is a radioactive marker selected from the group consisting of $^{32}P$, $^{14}C$, $^{3}H$, $^{125}I$ and $^{35}S$.

47. The HPV hybridization probe composition as claimed in claim 42, wherein at least any one of said marker is a non-radioactive marker selected from the group consisting of biotin, an enzyme and a fluorescent molecule.

48. The HPV hybridization probe composition as claimed in claim 47, wherein said enzyme is selected from the group consisting of alkaline phosphatase and horseradish peroxidase.

49. The HPV hybridization probe composition as claimed in claim 47, wherein said fluorescent molecule is selected from the group consisting of fluorescein and rhodamine.

50. The HPV hybridization probe composition as claimed in claim 42, wherein said other HPV type is at least one member selected from the group consisting of HPV 6, HPV 11, HPV 16, HPV 18 and HPV 31.

51. The HPV hybridization probe composition as claimed in claim 50, wherein said other HPV type is at least one member selected from the group consisting of HPV 16, HPV 18 and HPV 31.

52. The HPV hybridization probe composition as claimed in claim 51, wherein said other HPV type is HPV 16, HPV 18 and HPV 31.

53. A method for detecting HPV DNA or RNA comprising:
  carrying out hybridization, under non-stringent conditions, with
    (a) a labelled HPV 35 nucleic acid selected from the group consisting of
      (i) HPV 35 DNA or fragments thereof labelled with a marker, and
      (ii) HPV 35 RNA or fragments thereof labelled with a marker;
    (b) an unknown sample of DNA or RNA, and
    (c) at least one other labelled HPV-type nucleic acid; and
  (2) assaying for the presence of cross-hybridization between all labelled nucleic acid and unknown sample so as to detect HPV DNA or RNA in said sample.

54. The method as claimed in claim 53, wherein said unknown sample of DNA or RNA is derived from a genital, throat, oral or skin lesion.

55. The method as claimed in claim 54, wherein said unknown sample of DNA or RNA is derived from a genital lesion.

56. The method as claimed in claim 55, wherein said unknown sample of DNA or RNA derived from a genital lesion is obtained by biopsying an epithelial lesion, scraping the cervix or by swabbing the cervix to obtain exfoliated cells or is DNA derived from a genital lesion which has been cloned in a cloning vector.

57. The method as claimed in claim 53, wherein at least any one of said fragments are about 15 to about 8000 bases or base pairs in size.

58. The method as claimed in claim 57, wherein at least any one of said fragments are about 300 to about 800 bases or base pairs in size.

59. The method as claimed in claim 53, wherein said at least one other labelled HPV-type nucleic is selected from the group consisting of:
  (i) HPV 6 DNA or fragments thereof labelled with a marker;
  (ii) HPV 6 RNA or fragments thereof labelled with a marker;
  (iii) HPV 11 DNA or fragments thereof labelled with a marker;
  (iv) HPV 11 RNA or fragments thereof labelled with a marker;
  (v) HPV 16 DNA or fragments thereof labelled with a marker;
  (vi) HPV 16 RNA or fragments thereof labelled with a marker;

(vii) HPV 18 DNA or fragments thereof labelled with a marker; and (viii) HPV 18 RNA or fragments thereof labelled with a marker.

60. The method as claimed in claim 59, wherein said other HPV type is at least one member selected from the group consisting of HPV 16 and HPV 18.

61. The method as claimed in claim 60, wherein said other HPV type is HPV 16 and HPV 18.

62. The method as claimed in claim 53, wherein at least any one of said marker is a radioactive marker.

63. The method as claimed in claim 62, wherein at least any one of said marker is a radioactive marker selected from the group consisting of $^{32}P$, $^{14}C$, $^{3}H$, $^{125}I$ and $^{35}S$.

64. The method as claimed in claim 53, wherein at least any one of said marker is a non-radioactive marker selected from the group consisting of biotin, an enzyme and a fluorescent molecule.

65. The method as claimed in claim 64, wherein said enzyme is selected from the group consisting of alkaline phosphatase and horseradish peroxidase.

66. The method as claimed in claim 64, wherein said fluorescent molecule is selected from the group consisting of fluorescein and rhodamine.

67. The method as claimed in claim 53, wherein said cross-hybridization produces DNA-DNA hybrids.

68. The method as claimed in claim 53, wherein said cross-hybridization produces DNA-RNA hybrids.

69. A method for detecting HPV 35 DNA or RNA comprising:
(1) carrying out hybridization, under stringent conditions, with
(a) a member selected from the group consisting of
(i) HPV 35 DNA or fragments thereof labelled with a marker, and
(ii) HPV 35 RNA or fragments thereof labelled with a marker;
(b) an unknown sample of DNA or RNA, and
(2) assaying for the presence of cross-hybridization so as to detect HPV 35 DNA or RNA in said sample.

70. The method as claimed in claim 69, wherein said unknown sample of DNA or RNA is derived from a genital, throat, oral or skin lesion.

71. The method as claimed in claim 70, wherein said unknown sample of DNA or RNA is derived from a genital lesion.

72. The method as claimed in claim 71, wherein said unknown sample of DNA or RNA derived from a genital lesion is obtained by biopsying an epithelial lesion, scraping the cervix or by swabbing the cervix to obtain exfoliated cells or is DNA derived from a genital lesion which has been cloned in a cloning vector.

73. The method as claimed in claim 69, wherein said fragments are about 15 to about 8000 bases or base pairs in size.

74. The method as claimed in claim 73, wherein said fragments are about 300 to about 800 bases or base pairs in size.

75. The method as claimed in claim 69, wherein said HPV 35 DNA comprises substantially all of the HPV 35 genome.

76. The method as claimed in claim 69, wherein said marker is a radioactive marker.

77. The method as claimed in claim 76, wherein said marker is a radioactive marker selected from the group consisting of $^{32}P$, $^{14}C$, $^{3}H$, $^{125}I$ and $^{35}S$.

78. The method as claimed in claim 69, wherein said marker is a non-radioactive marker selected from the group consisting of biotin, an enzyme and a fluorescent molecule.

79. The method as claimed in claim 78, wherein said enzyme is selected from the group consisting of alkaline phosphatase and horseradish peroxidase.

80. The method as claimed in claim 78, wherein said fluorescent molecule is selected from the group consisting of fluorescein and rhodamine.

81. The method as claimed in claim 69, wherein said cross-hybridization produces DNA-DNA hybrids.

82. The method as claimed in claim 69, wherein said cross-hybridization produces DNA-RNA hybrids.

83. A method for detecting HPV 35 DNA or RNA comprising:
(1) carrying out hybridization, under stringent conditions, with
(a) a first fraction of DNA or RNA derived from each individual genital lesion of a sampling of genital lesions, which sampling shows an epidemiological progression to cervical cancer, and
(b) a member selected from the group consisting of
(i) HPV 35 DNA or fragments thereof labelled with a marker, and
(ii) HPV 35 RNA or fragments thereof labelled with a marker;
and assaying for the presence of cross-hybridization with the DNA or RNA derived from each individual genital lesion of said sampling of genital lesions;
(2) carrying out hybridization, under stringent conditions, with
(a) a second fraction of DNA or RNA derived from each individual genital lesion of said sampling of genital lesions, and
(b) an unknown sample of DNA or RNA derived from a genital lesion which has been labelled with a marker;
and assaying for the presence of cross-hybridization with the DNA or RNA derived from each individual genital lesion of said sampling of genital lesions;
(3) comparing the overall patterns of cross-hybridization of said sampling of genital lesions obtained in Step (1) with that obtained in Step (2); and
(4) comparing the cross-hybridizations of each individual genital lesion of said sampling of genital lesions obtained in Step (1) with that obtained in Step (2);
wherein the presence of HPV 35 DNA or RNA in said unknown sample is detected when both (i) the overall patterns of cross-hybridization of said sampling of genital lesions are essentially the same, and (ii) the cross-hybridizations of each individual genital lesion of said sampling of genital lesions are essentially the same.

84. The method as claimed in claim 83, wherein said fragments are about 15 to about 8000 bases or base pairs in size.

85. The method as claimed in claim 84, wherein said fragments are about 300 to about 800 bases or base pairs in size.

86. The method as claimed in claim 83, wherein said HPV 35 DNA comprises substantially all of the HPV 35 genome.

87. The method as claimed in claim 83, wherein at least any one of said marker is a radioactive marker.

88. The method as claimed in claim 87, wherein at least any one of said marker is a radioactive marker selected from the group consisting of $^{32}P$, $^{14}C$, $^{3}H$, $^{125}I$ and $^{35}S$.

89. The method as claimed in claim 83, wherein at least any one of said marker is a non-radioactive marker selected from the group consisting of biotin, an enzyme and a fluorescent molecule.

90. The method as claimed in claim 89, wherein said enzyme is selected from the group consisting of alkaline phosphatase and horseradish peroxidase.

91. The method as claimed in claim 89, wherein said fluorescent molecule is selected from the group consisting of fluorescein and rhodamine.

92. The method as claimed in claim 83, wherein said unknown sample of DNA or RNA derived from a genital lesion is obtained by biopsying an epithelial lesion, scraping the cervix or by swabbing the cervix to obtain exfoliated cells or is DNA derived from a genital lesion which has been cloned in a cloning vector.

93. The method as claimed in claim 83, wherein at least any one of said cross-hybridization produces DNA-DNA hybrids.

94. The method as claimed in claim 83, wherein at least any one of said cross-hybridization produces DNA-RNA hybrids.

* * * * *